(12) United States Patent
Yanagawa et al.

(10) Patent No.: US 9,382,174 B2
(45) Date of Patent: Jul. 5, 2016

(54) METHOD FOR PRODUCING MONOCYCLIC AROMATIC HYDROCARBONS

(75) Inventors: Shinichiro Yanagawa, Tokyo (JP); Ryoji Ida, Tokyo (JP); Masahide Kobayashi, Tokyo (JP); Yasuyuki Iwasa, Tokyo (JP)

(73) Assignee: JX Nippon Oil & Energy Corporation, Tokyo (JP)

(*) Notice: Subject to any disclaimer, the term of this patent is extended or adjusted under 35 U.S.C. 154(b) by 246 days.

(21) Appl. No.: 14/007,193

(22) PCT Filed: Mar. 23, 2012

(86) PCT No.: PCT/JP2012/057537
§ 371 (c)(1),
(2), (4) Date: Nov. 15, 2013

(87) PCT Pub. No.: WO2012/133197
PCT Pub. Date: Oct. 4, 2012

(65) Prior Publication Data
US 2014/0066673 A1    Mar. 6, 2014

(30) Foreign Application Priority Data

Mar. 25, 2011  (JP) ................. 2011-067747

(51) Int. Cl.
*C07C 2/42* (2006.01)
*C07C 2/76* (2006.01)
(Continued)

(52) U.S. Cl.
CPC ... *C07C 5/10* (2013.01); *C07C 4/06* (2013.01); *C10G 11/18* (2013.01); *C10G 45/60* (2013.01);
(Continued)

(58) Field of Classification Search
CPC .............. C07C 2/42; C07C 2/76; C07C 5/11; C07C 57/00

USPC .......... 585/319, 418, 266, 268; 208/67, 62, 49
See application file for complete search history.

(56) References Cited

U.S. PATENT DOCUMENTS 3,755,141 A    8/1973  Youngblood et al.
3,806,443 A    4/1974  Maziuk
(Continued)

FOREIGN PATENT DOCUMENTS

EP    2351820 A2    8/2011
JP    S49-41323 A   4/1974
(Continued)

OTHER PUBLICATIONS

Extended European Search Report issued Aug. 4, 2014 in EP Application No. 12765326.9.
Int'l Search Report issued Jun. 5, 2012 in Int'l Application No. PCT/JP2012/057537.

*Primary Examiner* — Thuan D Dang
(74) *Attorney, Agent, or Firm* — Panitch Schwarze Belisario & Nadel LLP

(57) ABSTRACT

A method for producing monocyclic aromatic hydrocarbons includes a cracking reforming reaction step of bringing an oil feedstock into contact with a catalyst for monocyclic aromatic hydrocarbon production containing a crystalline aluminosilicate, and causing the oil feedstock to react, thereby obtaining a product containing monocyclic aromatic hydrocarbons having 6 to 8 carbon atoms, a hydrogenation reaction step of hydrogenating a product produced in the cracking reforming reaction step, a monocyclic aromatic hydrocarbon recovery step of recovering monocyclic aromatic hydrocarbons having 6 to 8 carbon atoms separated from a hydrogenation product obtained in the hydrogenation reaction step and a recycling step of returning a heavy fraction having 9 or more carbon atoms separated from the hydrogenation product obtained in the hydrogenation reaction step to the cracking reforming reaction step.

6 Claims, 2 Drawing Sheets

(51) Int. Cl.
*C07C 5/11* (2006.01)
*C07C 57/00* (2006.01)
*C07C 5/10* (2006.01)
*C10G 45/60* (2006.01)
*C10G 45/70* (2006.01)
*C10G 11/18* (2006.01)
*C07C 4/06* (2006.01)
*C10G 47/00* (2006.01)
*C10G 47/20* (2006.01)

(52) U.S. Cl.
CPC ................ *C10G 45/70* (2013.01); *C10G 47/00* (2013.01); *C10G 47/20* (2013.01); *C10G 2300/1044* (2013.01); *C10G 2300/1048* (2013.01); *C10G 2300/1051* (2013.01); *C10G 2300/1055* (2013.01); *C10G 2300/1096* (2013.01); *C10G 2300/4025* (2013.01); *C10G 2400/30* (2013.01)

(56) References Cited

U.S. PATENT DOCUMENTS

| | | | |
|---|---|---|---|
| 4,053,388 A | 10/1977 | Bailey | |
| 5,582,711 A | 12/1996 | Ellis et al. | |
| 8,912,377 B2 * | 12/2014 | Kim | C10G 11/02 585/256 |
| 2004/0215042 A1 * | 10/2004 | Bottcher | C07C 5/10 585/400 |

FOREIGN PATENT DOCUMENTS

| | | |
|---|---|---|
| JP | S53-116328 A | 10/1978 |
| JP | H03-002128 A | 1/1991 |
| JP | H03-026791 A | 2/1991 |
| JP | H03-052993 A | 3/1991 |
| JP | 2007-154151 A | 6/2007 |
| JP | 2009-235248 A | 10/2009 |
| JP | 2012-062255 A | 3/2012 |
| WO | 2010044562 A2 | 4/2010 |
| WO | 2011118753 A1 | 9/2011 |

* cited by examiner

METHOD FOR PRODUCING MONOCYCLIC AROMATIC HYDROCARBONS

CROSS-REFERENCE TO RELATED APPLICATION

This application is a Section 371 of International Application No. PCT/JP2012/057537, filed Mar. 23, 2012, which was published in the Japanese language on Oct. 4, 2012, under International Publication No. WO 2012/133197 A1, and the disclosure of which is incorporated herein by reference.

TECHNICAL FIELD

The present invention relates to a method for producing a monocyclic aromatic hydrocarbon.

Priority is claimed on Japanese Patent Application No. 2011-067747, filed Mar. 25, 2011, the contents of which are incorporated herein by reference.

BACKGROUND ART

Light cycle oil (hereinafter, referred to as "LCO"), which is cracked light oil produced with a fluid catalytic cracking (hereinafter, referred to as "FCC") unit, contains a large amount of polycyclic aromatic hydrocarbons, and have been utilized as diesel or fuel oil. However, in recent years, investigations have been conducted to obtain monocyclic aromatic hydrocarbons having 6 to 8 carbon atoms with a high added value (for example, benzene, toluene, xylene, and ethylbenzene) that can be utilized as high octane gasoline base materials or petroleum chemistry raw materials, from the LCO.

For example, in Patent Document 1 to Patent Document 3, there have been suggested methods for producing a monocyclic aromatic hydrocarbon from a polycyclic aromatic hydrocarbon that is contained in LCO or the like in a large amount, using a zeolite catalyst.

PRIOR ART DOCUMENTS

Patent Documents

[Patent Document 1] Japanese Unexamined Patent Application, First Publication No. H3-2128
[Patent Document 2] Japanese Unexamined Patent Application, First Publication No. H3-52993
[Patent Document 3] Japanese Unexamined Patent Application, First Publication No. H3-26791

DISCLOSURE OF INVENTION

Technical Problem

However, in the methods described in Patent Documents 1 to 3, it cannot be said that the yield of monocyclic aromatic hydrocarbons having 6 to 8 carbon atoms is sufficiently high.

The present invention was achieved in view of such circumstances, and an object of the invention is to provide a method for producing monocyclic aromatic hydrocarbons, which can produce monocyclic aromatic hydrocarbons having 6 to 8 carbon atoms with a high yield from an oil feedstock containing polycyclic aromatic hydrocarbons.

Solution to Problem

The present inventors repeated thorough studies in order to achieve the above object, and, consequently, obtained the following knowledge.

When an oil feedstock is supplied to a cracking reforming reaction step, a heavy fraction having 9 or more carbon atoms separated from a produced product is hydrogenated, and then an obtained hydrogenation product of the heavy fraction is returned to the cracking reforming reaction step, monocyclic aromatic hydrocarbons having 6 to 8 carbon atoms can be produced with a high yield.

In addition, the inventors further repeated studies based on the knowledge above, and, consequently, found that the thermal efficiency and the like can be further improved for production methods based on the knowledge, thereby completing the invention.

That is, a method for producing monocyclic aromatic hydrocarbons of a first aspect of the invention relates to a method for producing monocyclic aromatic hydrocarbons having 6 to 8 carbon atoms from an oil feedstock having a 10 vol % distillation temperature of 140° C. or higher and a 90 vol % distillation temperature of 380° C. or lower, the method including: a cracking reforming reaction step of bringing the oil feedstock into contact with a catalyst for monocyclic aromatic hydrocarbon production containing a crystalline aluminosilicate, and causing the oil feedstock to react, thereby obtaining a product containing monocyclic aromatic hydrocarbons having 6 to 8 carbon atoms; a hydrogenation reaction step of hydrogenating a product produced in the cracking reforming reaction step; a monocyclic aromatic hydrocarbon recovery step of recovering monocyclic aromatic hydrocarbons having 6 to 8 carbon atoms separated from a hydrogenation product obtained in the hydrogenation reaction step; and a recycling step of returning a heavy fraction having 9 or more carbon atoms separated from the hydrogenation product obtained in the hydrogenation reaction step to the cracking reforming reaction step.

In addition, the method for producing monocyclic aromatic hydrocarbons preferably further includes a raw material mixing step of mixing a portion of the oil feedstock with the product produced in the cracking reforming reaction step.

A method for producing monocyclic aromatic hydrocarbons of a second aspect of the invention relates to a method for producing monocyclic aromatic hydrocarbons having 6 to 8 carbon atoms from an oil feedstock having a 10 vol % distillation temperature of 140° C. or higher and a 90 vol % distillation temperature of 380° C. or lower, the method including: a hydrogenation reaction step of hydrogenating the oil feedstock; a monocyclic aromatic hydrocarbon recovery step of recovering monocyclic aromatic hydrocarbons having 6 to 8 carbon atoms separated from a hydrogenation product obtained in the hydrogenation reaction step; a recycling step of supplying a heavy fraction having 9 or more carbon atoms separated from the hydrogenation product obtained in the hydrogenation reaction step to the cracking reforming reaction step; and a reaction product supply step of supplying a product produced in the cracking reforming reaction step together with the oil feedstock to the hydrogenation reaction step, wherein, in the cracking reforming reaction step, the heavy fraction having 9 or more carbon atoms is brought into contact with a catalyst for monocyclic aromatic hydrocarbon production containing a crystalline aluminosilicate, and caused to react, thereby producing a product containing monocyclic aromatic hydrocarbons having 6 to 8 carbon atoms.

In addition, in the method for producing monocyclic aromatic hydrocarbons, the crystalline aluminosilicate contained in the catalyst for monocyclic aromatic hydrocarbon production used in the cracking reforming reaction step preferably contain a medium-pore zeolite and/or a large-pore zeolite as main components.

In addition, the method for producing monocyclic aromatic hydrocarbons preferably further includes a hydrogen recovery step of recovering hydrogen produced as a by-product in the cracking reforming reaction step from the hydrogenation product obtained in the hydrogenation reaction step, and a hydrogen supply step of supplying the hydrogen collected in the hydrogen recovery step to the hydrogenation reaction step.

Advantageous Effects of Invention

According to the method for producing monocyclic aromatic hydrocarbons of the invention, monocyclic aromatic hydrocarbons having 6 to 8 carbon atoms can be produced from an oil feedstock containing polycyclic aromatic hydrocarbons with a high yield.

In addition, for example, as described in the knowledge above, in the case where the raw material is supplied to the cracking reforming reaction step and the heavy fraction having 9 or more carbon atoms separated from the produced product is hydrogenated, since the heavy fraction having 9 or more carbon atoms is reheated in the hydrogenation reaction step after once cooled, when the heavy fraction having 9 or more carbon atoms is separated, thermal loss is caused, and the thermal efficiency decreases. In contrast to what has been described above, in the invention, since the heavy fraction is not separated in the former phase of the hydrogenation reaction step and begins to be separated in the latter phase of the hydrogenation reaction step as compared with the case where the heavy fraction is separated followed by the hydrogenation reaction being carried out, the thermal efficiency can be increased by reducing the thermal loss. Additionally, regarding heat generation during the hydrogenation, which is a problem when the heavy fraction having a high concentration of polycyclic aromatic hydrocarbons and 9 or more carbon atoms is hydrogenated, the concentration of polycyclic aromatic hydrocarbons is decreased by hydrogenating monocyclic aromatic hydrocarbons without separation, and heat generation can be suppressed in the hydrogenation reaction step.

BEST MODE FOR CARRYING OUT THE INVENTION

Embodiment 1

Hereinafter, Embodiment 1 of the method for producing monocyclic aromatic hydrocarbons of the invention will be described.

Figure 1:
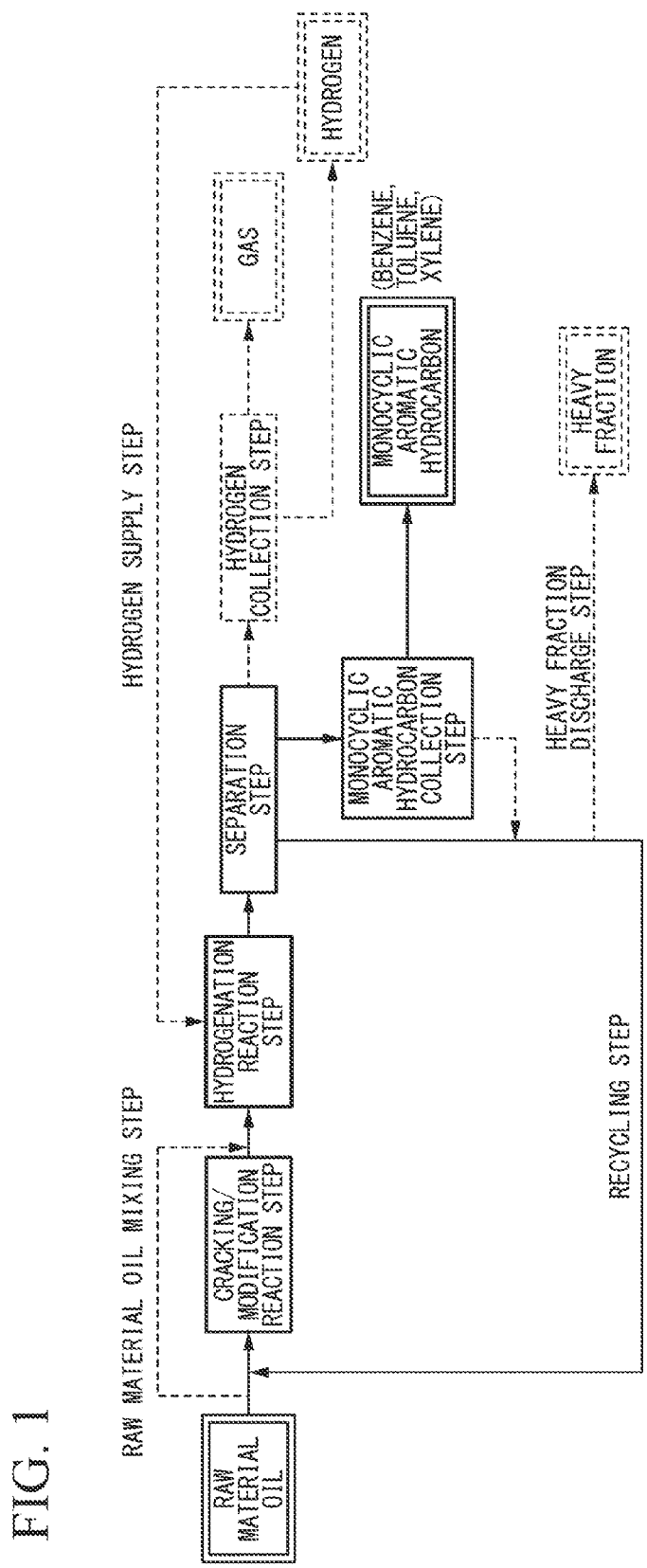
FIG. 1 is a diagram for illustrating Embodiment 1 of the method for producing monocyclic aromatic hydrocarbons of the invention.

FIG. 1 is a diagram for illustrating Embodiment 1 of the method for producing monocyclic aromatic hydrocarbons of the invention. The method for producing monocyclic aromatic hydrocarbons of the present Embodiment is a method of producing monocyclic aromatic hydrocarbons having 6 to 8 carbon atoms from an oil feedstock.

That is, the method for producing monocyclic aromatic hydrocarbons of the present Embodiment, as illustrated in FIG. 1, preferably includes:

(a) a cracking reforming reaction step of bringing an oil feedstock into contact with a catalyst for monocyclic aromatic hydrocarbon production, and causing the oil feedstock to react, thereby obtaining a product containing monocyclic aromatic hydrocarbons having 6 to 8 carbon atoms;

(b) a hydrogenation reaction step of hydrogenating the product produced in the cracking reforming reaction step;

(c) a separation step of separating a hydrogenation product obtained in the hydrogenation reaction step into plural fractions;

(d) a monocyclic aromatic hydrocarbon recovery step of recovering the monocyclic aromatic hydrocarbons having 6 to 8 carbon atoms separated in the separation step;

(e) a heavy fraction discharge step of discharging a portion of a heavy fraction having 9 or more carbon atoms (hereinafter, referred to simply as a "heavy fraction") separated in the separation step out of a system;

(f) a recycling step of returning the heavy fraction not discharged out of the system in the heavy fraction discharge step to the cracking reforming reaction step;

(g) a hydrogen recovery step of recovering hydrogen produced as a by-product in the cracking reforming reaction step from a gas component separated in the separation step; and (h) a hydrogen supply step of supplying the hydrogen collected in the hydrogen recovery step to the hydrogenation reaction step.

Among the steps (a) to (h), the steps (a), (b), (d), and (f) are essential steps for the Embodiment 1, and the steps (c), (e), (g), and (h) are optional steps.

Hereinafter, the respective steps will be described in detail.

<Cracking Reforming Reaction Step>

In the cracking reforming reaction step, an oil feedstock is brought into contact with a catalyst for monocyclic aromatic hydrocarbon production, and using saturated hydrocarbons contained in the oil feedstock as a hydrogen donating source, polycyclic aromatic hydrocarbons are partially hydrogenated by a hydrogen transfer reaction from the saturated hydrocarbons. Thus, ring-opening is carried out, and thereby the polycyclic aromatic hydrocarbons are converted to monocyclic aromatic hydrocarbons. Furthermore, the saturated hydrocarbons that are present in the oil feedstock or are obtainable in the hydrogenation reaction step can also be converted to monocyclic aromatic hydrocarbons through cyclization and dehydrogenation. Also, monocyclic aromatic hydrocarbons having 6 to 8 carbon atoms can also be obtained by cracking monocyclic aromatic hydrocarbons having 9 or more carbon atoms. Thereby, a product containing monocyclic aromatic hydrocarbons having 6 to 8 carbon atoms and a heavy fraction having 9 or more carbon atoms is obtained.

This product includes, in addition to the monocyclic aromatic hydrocarbons and the heavy fraction, hydrogen, methane, ethane, ethylene, LPG (propane, propylene, butane, butene and the like), and the like. Furthermore, the heavy fraction includes a large amount of bicyclic aromatic hydrocarbons such as naphthalene, methylnaphthalene and dimethylnaphthalene, and also, aromatic hydrocarbons having three or more rings, such as anthracene, may also be included depending on the oil feedstock. In the present application, these bicyclic aromatic hydrocarbons and aromatic hydrocarbons having three or more rings are collectively described as polycyclic aromatic hydrocarbons.

In this cracking reforming reaction step, regarding components such as naphthenobenzenes, paraffins and naphthenes in the oil feedstock, a majority of the components are lost by producing monocyclic aromatic hydrocarbons. Furthermore, regarding polycyclic aromatic hydrocarbons, a portion thereof is converted to naphtaenobenzenes and then monocyclic aromatic hydrocarbons by cracking and hydrogen transfer with saturated hydrocarbons, but at the same time, as alkyl side chains are cleaved, bicyclic aromatic hydrocarbons having fewer side chains, such as naphthalene, methylnaphthalene and dimethylnaphthalene, are also mainly produced as by-products. Therefore, in this cracking reforming reaction step, monocyclic aromatic hydrocarbons are produced with a high yield, and at the same time, bicyclic aromatic hydrocarbons are also produced as by-products as a heavy fraction having 9 or more carbon atoms.

(Oil Feedstock)

The oil feedstock used in the present Embodiment is an oil having a 10 vol % distillation temperature of 140° C. or higher and a 90 vol % distillation temperature of 380° C. or lower. If an oil having a 10 vol % distillation temperature of lower than 140° C. is used, monocyclic aromatic hydrocarbons are produced from a light oil feedstock, and this does not fit into the main object of the present embodiment. Furthermore, in the case of using an oil having a 90 vol % distillation temperature higher than 380° C., the yield of monocyclic aromatic hydrocarbons is decreased, the amount of coke deposition on the catalyst for monocyclic aromatic hydrocarbon production increases, and a rapid decrease in the catalyst activity tends to occur.

The 10 vol % distillation temperature of the oil feedstock is preferably 150° C. or higher, and the 90 vol % distillation temperature of the oil feedstock is preferably 360° C. or lower.

In addition, the 10 vol % distillation temperature and the 90 vol % distillation temperature as used herein mean values measured according to JIS K2254 "Petroleum products—Distillation Testing Methods."

Examples of oil feedstocks having a 10 vol % distillation temperature of 140° C. or higher and a 90 vol % distillation temperature of 380° C. or lower include LCO, hydrogenation purified oil of LCO, coal liquefaction oil, heavy oil hydrocracking purified oil, straight run kerosene, straight run gas oil, coker kerosene, coker gas oil, and oil sand hydrocracking purified oil.

Since polycyclic aromatic hydrocarbons have a low reactivity, the polycyclic aromatic hydrocarbons are not easily converted to monocyclic aromatic hydrocarbons in the cracking reforming reaction step of the present Embodiment, and a portion of the polycyclic aromatic hydrocarbons remain in the product. However, since polycyclic aromatic hydrocarbons are hydrogenated in the hydrogenation reaction step that will be described below, and are converted to naphthenobenzenes, and then the naphthenobenzenes are supplied to the cracking reforming reaction step for recycling, the polycyclic aromatic hydrocarbons can be easily converted to monocyclic aromatic hydrocarbon. Therefore, the oil feedstock is not particularly limited in view of containing a large amount of polycyclic aromatic hydrocarbons. However, among the polycyclic aromatic hydrocarbons, aromatic hydrocarbons having three or more rings consume a large amount of hydrogen in the hydrogenation reaction step, and the reactivity of hydrogenation products thereof in the cracking reforming reaction step is low, thereby it is not preferable for the oil feedstock to contain a large amount of the polycyclic aromatic hydrocarbons having three or more rings. Therefore, the content of aromatic hydrocarbons having three or more rings in the oil feedstock is preferably 25 vol % or less, and more preferably 15 vol % or less.

In addition, regarding the oil feedstock containing bicyclic aromatic hydrocarbons that are converted to naphthenobenzene in the hydrogenation reaction step and intended to reduce aromatic hydrocarbons having three or more rings, for example, it is more preferable that the 90 vol % distillation temperature of the oil feedstock be 330° C. or lower.

Furthermore, the polycyclic aromatic hydrocarbons as used herein mean the total value of the content of bicyclic aromatic hydrocarbons (bicyclic aromatic fraction) and the content of aromatic hydrocarbons having three or more rings (tricyclic or higher-cyclic aromatic fraction) that are measured according to JPI-5S-49 "Petroleum products—Hydrocarbon type test methods—High performance liquid chromatography method", or analyzed by an FID gas chromatographic method or a two-dimensional gas chromatographic method. Hereinafter, when the contents of polycyclic aromatic hydrocarbons, bicyclic aromatic hydrocarbons, and aromatic hydrocarbons having three or more rings are expressed in vol %, the contents are values measured according to JPI-5S-49, and when the contents are expressed in mass %, the values are measured based on an FID gas chromatographic method or a two-dimensional gas chromatographic method.

(Reaction Type)

Regarding the reaction type at the time of bringing the oil feedstock into contact with a catalyst for monocyclic aromatic hydrocarbon production and causing the oil feedstock to react, examples thereof include a fixed bed, a moving bed, and a fluidized bed. In this Embodiment, since a heavy fraction is used as the raw material, a fluidized bed in which the coke fraction adhered to the catalyst can be continuously removed and the reaction can be carried out in a stable manner, is preferred, and a continuous regeneration type fluidized bed in which a catalyst is circulated between a reactor and a regenerator and thus reaction and regeneration can be continuously repeated, is particularly preferred. The oil feedstock at the time of being brought into contact with the catalyst for monocyclic aromatic hydrocarbon production is preferably in a gaseous state. Furthermore, the raw material may be diluted by means of a gas as necessary.

(Catalyst for Monocyclic Aromatic Hydrocarbon Production)

The catalyst for monocyclic aromatic hydrocarbon production contains a crystalline aluminosilicate.

[Crystalline Aluminosilicate]

The crystalline aluminosilicate is preferably a medium-pore zeolite and/or a large-pore zeolite, from the viewpoint that the yield of monocyclic aromatic hydrocarbons can be further increased. Additionally, examples of the "medium-pore zeolite and/or large-pore zeolite" as used herein include zeolites containing a medium-pore zeolite or a large-pore zeolite as main components.

A medium-pore zeolite is a zeolite having a 10-membered ring skeletal structure, and examples of the medium-pore zeolite include zeolites having crystal structures of AEL type, EUO type, FER type, HEU type, MEL type, MFI type, NES type, TON type, and WEI type. Among these, from the viewpoint of further increasing the yield of monocyclic aromatic hydrocarbons, MFI type is preferred.

A large-pore zeolite is a zeolite having a 12-membered ring skeletal structure, and examples of the large-pore zeolite include zeolites having crystal structures of AFI type, ATO type, BEA type, CON type, FAU type, GME type, LTL type, MOR type, MTW type, and OFF type. Among these, from the viewpoint of being industrially usable, zeolites of BEA type, FAU type and MOR type are preferred, and from the viewpoint of further increasing the yield of monocyclic aromatic hydrocarbons, a zeolite of BEA type is preferred.

The crystalline aluminosilicate may contain a small-pore zeolite having a 10-membered or fewer-membered ring skeletal structure, or an ultralarge-pore zeolite having a 14-membered or more-membered ring skeletal structure, in addition to the medium-pore zeolite and the large-pore zeolite.

Here, examples of the small-pore zeolite include zeolites having crystal structures of ANA type, CHA type, ERI type, GIS type, KFI type, LTA type, NAT type, PAU type, and YUG type.

Examples of the ultralarge-pore zeolite include zeolites having crystal structures of CLO type and VPI type.

When the cracking reforming reaction step is carried out by a fixed bed reaction, the content of the crystalline aluminosilicate in the catalyst for monocyclic aromatic hydrocarbon production is preferably 60 mass % to 100 mass %, more preferably 70 mass % to 100 mass %, and particularly preferably 90 mass % to 100 mass %, when the total amount of the catalyst for monocyclic aromatic hydrocarbon production is designated as 100 mass %. If the content of the crystalline aluminosilicate is 60 mass % or more, the yield of monocyclic aromatic hydrocarbons can be sufficiently increased.

When the cracking reforming reaction step is carried out by a fluidized bed reaction, the content of the crystalline aluminosilicate in the catalyst for monocyclic aromatic hydrocarbon production is preferably 20 mass % to 60 mass %, more preferably 30 mass % to 60 mass %, and particularly preferably 35 mass % to 60 mass %, when the total amount of the catalyst for monocyclic aromatic hydrocarbon production is designated as 100 mass %. If the content of the crystalline aluminosilicate is 20 mass % or more, the yield of monocyclic aromatic hydrocarbons can be sufficiently increased. If the content of the crystalline aluminosilicate is more than 60 mass %, the content of the binder that can be incorporated into the catalyst is reduced, and the catalyst may become unsuitable for fluidized bed applications.

[Gallium and Zinc]

The catalyst for monocyclic aromatic hydrocarbon production can contain gallium and/or zinc as necessary. When gallium and/or zinc is incorporated, the production proportion of the monocyclic aromatic hydrocarbons can be further increased.

Examples of the form of gallium incorporation in the catalyst for monocyclic aromatic hydrocarbon production include a form in which gallium is incorporated into the lattice skeleton of the crystalline aluminosilicate (crystalline aluminogallosilicate), a form in which gallium is supported on the crystalline aluminosilicate (gallium-supported crystalline aluminosilicate), and a form including both.

Examples of the form of zinc incorporation in the catalyst for monocyclic aromatic hydrocarbon production include a form in which zinc is incorporated into the lattice skeleton of the crystalline aluminosilicate (crystalline aluminozincosilicate), a form in which zinc is supported in the crystalline aluminosilicate (zinc-supported crystalline aluminosilicate), and a form including both.

A crystalline aluminogallosilicate and a crystalline aluminozincosilicate have a structure in which $SiO_4$, $AlO_4$ and $GaO_4/ZnO_4$ structures exist in the skeleton. Furthermore, the crystalline aluminogallosilicate and crystalline aluminozincosilicate are obtained by, for example, gel crystallization based on hydrothermal synthesis, a method of inserting gallium or zinc into the lattice skeleton of a crystalline aluminosilicate, or a method of inserting aluminum into the lattice skeleton of a crystalline gallosilicate or a crystalline zincosilicate.

A gallium-supported crystalline aluminosilicate is a material in which gallium is supported on a crystalline aluminosilicate according to a known method such as an ion exchange method or an impregnation method. The gallium source used at that time is not particularly limited, but examples thereof include gallium salts such as gallium nitrate and gallium chloride, and gallium oxide.

A zinc-supported crystalline aluminosilicate is a material in which zinc is supported on a crystalline aluminosilicate according to a known method such as an ion exchange method or an impregnation method. The zinc source used at that time is not particularly limited, but examples thereof include zinc salts such as zinc nitrate and zinc chloride, and zinc oxide.

When the catalyst for monocyclic aromatic hydrocarbon production contains gallium and/or zinc, the content of gallium and/or zinc in the catalyst for monocyclic aromatic hydrocarbon production is preferably 0.01 to 5.0 mass %, and more preferably 0.05 to 2.0 mass %, when the total amount of the catalyst is designated as 100 mass %. If the content of gallium and/or zinc is 0.01 mass % or more, the production proportion of the monocyclic aromatic hydrocarbons can be further increased, and if the content is 5.0 mass % or less, the yield of the monocyclic aromatic hydrocarbons can be further increased.

[Phosphorus and Boron]

For the catalyst for monocyclic aromatic hydrocarbon production, it is preferable that the catalyst contain phosphorus and/or boron. When the catalyst for monocyclic aromatic hydrocarbon production contains phosphorus and/or boron, a decrease over time in the yield of the monocyclic aromatic hydrocarbons can be prevented, and coke production at the catalyst surface can be suppressed.

Examples of the method for incorporating phosphorus into the catalyst for monocyclic aromatic hydrocarbon production include a method of supporting phosphorus on a crystalline aluminosilicate, a crystalline aluminogallosilicate, or a crystalline aluminozincosilicate by means of an ion exchange method, an impregnation method or the like; a method of incorporating a phosphorus compound at the time of zeolite synthesis, and thereby substituting a portion in the skeleton of a crystalline aluminosilicate with phosphorus; and a method of using a crystallization accelerator containing phosphorus at the time of zeolite synthesis. The phosphate ion-containing aqueous solution to be used at that time is not particularly limited, but aqueous solutions prepared by dissolving phosphoric acid, diammonium hydrogen phosphate, ammonium dihydrogen phosphate, and other water-soluble phosphoric acid salts in water at arbitrary concentrations can be preferably used.

Examples of the method for incorporating boron into the catalyst for monocyclic aromatic hydrocarbon production include a method of supporting boron on a crystalline aluminosilicate, a crystalline aluminogallosilicate, or a crystalline aluminozincosilicate by means of an ion exchange method, an impregnation method or the like; a method of incorporating a boron compound at the time of zeolite synthesis and thereby substituting a portion in the skeleton of a crystalline aluminosilicate with boron; and a method of using a crystallization accelerator containing boron at the time of zeolite synthesis.

The content of phosphorus and/or boron in the catalyst for monocyclic aromatic hydrocarbon production is preferably 0.1 to 10 mass % with respect to the total mass of the catalyst, and it is more preferable to set the lower limit to 0.5 mass % or more and the upper limit to 9 mass % or less, and more preferably 8 mass % or less. When the content of phosphorus is 0.1 mass % or more with respect to the total mass of the catalyst, a decrease over time in the yield of monocyclic aromatic hydrocarbons can be prevented, and, when the content is 10 mass % or less, the yield of the monocyclic aromatic hydrocarbons can be increased.

[Shape]

The catalyst for monocyclic aromatic hydrocarbon production is formed into, for example, a powder form, a particulate form, or a pellet form, depending on the reaction type. For example, in the case of a fluidized bed, the catalyst is formed in a powder form, and in the case of a fixed bed, the catalyst is formed into a particulate form or a pellet form. The average particle size of the catalyst used in a fluidized bed is preferably 30 to 180 µm, and more preferably 50 to 100 µm. Furthermore, the apparent density of the catalyst used in a fluidized bed is preferably 0.4 to 1.8 g/cc, and more preferably 0.5 to 1.0 g/cc.

In addition, the average particle size represents a particle size which corresponds to 50 mass % in a particle size distribution obtained by classification with sieves, and the apparent density is a value measured by the method of JIS Standard R9301-2-3.

In the case of obtaining a particulate or pellet-shaped catalyst, according to necessity, an inert oxide is incorporated into the catalyst as a binder, and then the blend may be molded using various molding machines.

When the catalyst for monocyclic aromatic hydrocarbon production contains an inorganic oxide such as a binder, a binder containing phosphorus may be used without any problem.

(Reaction Temperature)

The reaction temperature at the time of bringing oil feedstock into contact with a catalyst for monocyclic aromatic hydrocarbon production and causing the oil feedstock to react is not particularly limited, but the reaction temperature is preferably set to 400 to 650° C. If the lower limit of the reaction temperature is 400° C. or higher, the oil feedstock can be made to react easily, and the lower limit is more preferably 450° C. or higher. Furthermore, if the upper limit of the reaction temperature is 650° C. or lower, the yield of the monocyclic aromatic hydrocarbons can be sufficiently increased, and the upper limit is more preferably 600° C. or lower.

(Reaction Pressure)

The reaction pressure at the time of bringing oil feedstock into contact with a catalyst for monocyclic aromatic hydrocarbon production and causing the oil feedstock to react is preferably set to 1.5 MPaG or less, and more preferably set to 1.0 MPaG or less. If the reaction pressure is 1.5 MPaG or less, production of by-products of light gas can be suppressed, and also, pressure resistance of the reaction apparatus can be lowered.

(Contact Time)

In regard to the contact time for the oil feedstock and the catalyst for monocyclic aromatic hydrocarbon production, there are no particular limitations as long as a desired reaction substantially proceeds; however, for example, the contact time as the time for gas passage on the catalyst for monocyclic aromatic hydrocarbon production is preferably 1 to 300 seconds, and it is more preferable to set the lower limit to 5 seconds or longer and the upper limit to 150 seconds or shorter. If the contact time is 1 second or longer, the reaction can be carried out reliably, and if the contact time is 300 seconds or shorter, accumulation of carbonaceous materials on the catalyst due to coking or the like can be suppressed. Also, the amount of generation of light gas due to cracking can be suppressed.

<Hydrogenation Reaction Step>

In the hydrogenation reaction step, the product produced in the cracking reforming reaction step is hydrogenated.

Specifically, the product is supplied to a hydrogenation reactor, and at least a portion of the polycyclic aromatic hydrocarbons contained in the product are, similarly, hydrogenation-treated by hydrogen contained in the product using a hydrogenation catalyst. That is, in the present Embodiment, it becomes possible to use hydrogen in the product produced in the cracking reforming reaction step.

In the case where attempts are made to convert polycyclic aromatic hydrocarbons in the heavy fraction to monocyclic naphthenebenzene using hydrogen produced in the cracking reforming reaction step, generally, since separation loss occurs in a step of separating and recovering the produced hydrogen from gas, it is difficult to use all the produced hydrogen for hydrogenation. Therefore, in the case where the produced hydrogen is more efficiently used in the hydrogenation reaction step, it is preferably to directly use the hydrogen in the hydrogenation reaction step without separating and recovering the hydrogen. In the reaction product of the cracking reforming reaction step, light hydrocarbons, such as methane and ethane, are also mixed in together with hydrogen. Therefore, since the hydrogen partial pressure relatively decreases with respect to the hydrogenation reaction pressure, the reaction product can be directly hydrogenated by optimizing the reaction conditions in the hydrogenation reaction step, such as, appropriately increasing the pressure depending on the composition and the like of the reaction product.

In the case where the amount of hydrogen produced in the cracking reforming reaction step and the like are small compared with polycyclic aromatic hydrocarbons, in order to more appropriately hydrogenate polycyclic aromatic hydrocarbons, it is also possible to supply hydrogen from an external source as necessary or to collect hydrogen produced in a series of steps and, again, supply the hydrogen to the hydrogenation reaction step. Even in that case, it is effective to directly supply the reaction product obtained in the cracking reforming reaction step to the hydrogenation reaction step as described in the present application from the viewpoint that the hydrogen produced in the cracking reforming reaction step is efficiently used without being separated.

The production method of the present Embodiment may be valuable since reaction heat necessary for the hydrogenation reaction step is efficiently used. For example, in the case where the reaction temperature in the cracking reforming reaction step is set to approximately 50 to 400° C. higher than in the hydrogenation reaction step, it becomes possible to more efficiently use the heat used in the cracking reforming reaction step in the hydrogenation reaction step as well. However, in the case where a method of causing the hydrogenation reaction after the separation step is employed, it is necessary to decrease the temperature of a fluid once for separation and then, again, prepare the temperature necessary for the hydrogenation reaction. However, according to the production method of the present Embodiment, it becomes possible to more efficiently use heat by directly supplying the reaction product obtained in the cracking reforming reaction step to the hydrogenation reaction step, and thermal loss can be suppressed at the minimum level.

As described above, since the polycyclic aromatic hydrocarbons in the oil feedstock have a low reactivity, in the cracking reforming reaction step, it is difficult to convert the polycyclic aromatic hydrocarbons to monocyclic aromatic hydrocarbons in the cracking reforming reaction step, and therefore the majority of the polycyclic aromatic hydrocarbons to the hydrogenation reaction step. That is, the product supplied to the hydrogenation reaction step contains a large amount of bicyclic aromatic hydrocarbons (polycyclic aromatic hydrocarbons) such as naphthalenes.

Thus, in the hydrogenation reaction step, it is preferable to hydrogenate these polycyclic aromatic hydrocarbons until the hydrocarbons each have one aromatic ring or less. For example, naphthalene is preferably hydrogenated until it becomes tetraline (naphthenobenzene), and also, alkylnaphthalenes such as methylnaphthalene and dimethylnaphthalene are preferably converted to naphthenobenzene, that is, an aromatic hydrocarbon having one aromatic ring and having a tetraline skeleton. Similarly, indenes are preferably converted to aromatic hydrocarbons having an indane skeleton, anthracenes are preferably converted to aromatic hydrocarbons having an octahydroanthracene skeleton, and phenanthrenes are preferably converted to aromatic hydrocarbons having an octahydrophenanthrene skeleton.

If the polycyclic aromatic hydrocarbons are hydrogenated until the hydrocarbons each have one aromatic ring or less, when a heavy fraction which passes through the separation step that will be described below and is separated from the hydrogenation product in the recycling step is returned to the cracking reforming reaction step, the hydrogenation products, particularly, aromatic hydrocarbons having a tetralin skeleton are easily converted to monocyclic aromatic hydrocarbons.

Regarding the hydrogenation product obtained in the hydrogenation reaction step, it is preferable to make the content of the polycyclic aromatic hydrocarbons in the heavy fraction having 9 or more carbon atoms separated in the separation step that will be described below smaller than the content of the polycyclic aromatic hydrocarbons in the oil feedstock. Regarding the content of the polycyclic aromatic hydrocarbons in the hydrogenation product, that is, the concentration of the polycyclic aromatic hydrocarbons, the concentration can be decreased by increasing the amount of the hydrogenation catalyst or increasing the reaction pressure.

However, it is not necessary to carry out the hydrogenation treatment until all of the polycyclic aromatic hydrocarbons become saturated hydrocarbons. Excessive hydrogenation brings about an increase in the amount of hydrogen consumption, and also causes an excessive increase in the amount of heat generation.

In the case where the product obtained in the cracking reforming reaction step is hydrogenated without being separated, compared with the case where only the heavy fraction is hydrogenated, the concentration of the polycyclic aromatic hydrocarbons becomes smaller than the concentration of the monocyclic aromatic hydrocarbons included in the product, and there is also an effect of relatively suppressing heat generation.

Regarding the reaction type in the hydrogenation reaction step, a fixed bed is suitably employed.

Regarding the hydrogenation catalyst, known hydrogenation catalysts (for example, nickel catalysts, palladium catalysts, nickel-molybdenum-based catalysts, cobalt-molybdenum-based catalysts, nickel-cobalt-molybdenum-based catalysts, and nickel-tungsten-based catalysts) can be used.

The hydrogenation reaction temperature may vary depending on the hydrogenation catalyst used, but the hydrogenation reaction temperature is considered to be usually in the range of 100 to 450° C., more preferably 200 to 400° C., and even more preferably 250 to 380° C. As described above, since the hydrogenation reaction temperature is 100 to 450° C. while the reaction temperature in the cracking reforming reaction step is 400 to 650° C., in the hydrogenation reaction step, it is not necessary to reheat the product obtained in the cracking reforming reaction step, and therefore thermal loss does not occur.

Regarding the hydrogenation reaction pressure, in the case where the gas in the hydrogenation reactor is considered to be 100% of the hydrogen concentration (hydrogen purity), the gas pressure is preferably set to from 2 to 15 MPa. Particularly, the gas pressure is more preferably set to from 2 to 12 MPa, and even more preferably set to from 3 to 10 MPa. If the hydrogenation reaction pressure is set to 15 MPa or less, a hydrogenation reactor having a relatively low durable pressure can be used, and the facility cost can be reduced. On the other hand, if the gas pressure is set to 2 MPa or higher, the yield of the hydrogenation reaction can be maintained sufficiently appropriately.

Additionally, the product produced in the cracking reforming reaction step contains gases such as methane or ethane in addition to hydrogen as described above. Therefore, while also varying depending on the composition of the oil feedstock, the reaction conditions in the cracking reforming reaction step, and the like, the hydrogen concentration (hydrogen purity) of gas in the product becomes 30 to 70 mol % (molar fraction). Therefore, it is desirable to regulate the reaction pressure in the hydrogenation reactor into which the product has been introduced so that the partial pressure of hydrogen in the gas in the reactor is from 2 to 15 MPa, more preferably 2 to 12 MPa, and even more preferably 3 to 10 MPa as described above. For example, in the case where the hydrogen concentration of gas in the reactor is 50 mol % (molar fraction) and there is an intention to set the hydrogenation reaction pressure (the gas pressure when the hydrogen concentration is considered to be 100%) to 4 MPa, the pressure (the actual hydrogenation reaction pressure) of gas in the reactor is set to 8 MPa. Thereby, the partial pressure of hydrogen can be set to 4 MPa, and the substantial hydrogenation reaction pressure (the gas pressure when the hydrogen concentration is considered to be 100%) becomes 4 MPa. Examples of the method for regulating the pressure of gas in the reactor include the supply of hydrogen to the hydrogenation reactor using the hydrogen supply step that will be described below. In addition, examples thereof include the supply of hydrogen from the outside of the system and, conversely, the supply of gases other than hydrogen from the outside of the system.

The amount of hydrogen consumption is preferably 2000 scfb (337 Nm$^3$/m$^3$) or less, more preferably 1500 scfb (253 Nm$^3$/m$^3$) or less, and even more preferably 1000 scfb (169 Nm$^3$/m$^3$) or less.

On the other hand, the amount of hydrogen consumption is preferably 100 scfb (17 Nm$^3$/m$^3$) or more in view of the yield of the hydrogenation reaction.

The liquid hourly space velocity (LHSV) is preferably set to from 0.1 to 20 and more preferably from 0.2 to 10 h$^{-1}$. If the LHSV is set to 20 h$^{-1}$ or less, polycyclic aromatic hydrocarbons can be sufficiently hydrogenated at a lower hydrogenation reaction pressure. On the other hand, when the LHSV is set to 0.1$^{-1}$ or more, an increase in the scale of the hydrogenation reactor can be avoided.

<Separation Step>

In the separation step, the hydrogenation product obtained in the hydrogenation reaction step is separated into multiple fractions.

In order to separate the hydrogenation product into multiple fractions, known distillation apparatuses and gas-liquid separation apparatuses may be used. An example of the distillation apparatuses may be an apparatus capable of separation by distillation into multiple fractions by means of a multistage distillation apparatus such as a stripper. An example of the gas-liquid separation apparatus may be an apparatus including a gas-liquid separation tank; a product inlet pipe through which the product is introduced into the gas-liquid separation tank; a gas component outflow pipe that is provided in the upper part of the gas-liquid separation tank; and a liquid component outflow pipe that is provided in the lower part of the gas-liquid separation tank.

In the separation step, at least a gas component and a liquid fraction are separated, and also, the liquid fraction is further separated into plural fractions. Examples of such a separation step include a form of separating the product into a gas component mainly containing components having 4 or fewer carbon atoms (for example, hydrogen, methane, ethane, and LPG) and a liquid fraction; a form of separating the product into a gas component containing components having 2 or fewer carbon atoms (for example, hydrogen, methane, and ethane) and a liquid fraction; a form of further separating the liquid fraction into a fraction containing monocyclic aromatic hydrocarbons and a heavy fraction; a form of separating the liquid fraction again into LPG, a fraction containing monocyclic aromatic hydrocarbons, and a heavy fraction; and a form of separating the liquid fraction again into LPG, a fraction containing monocyclic aromatic hydrocarbons, and plural heavy fractions.

In this Embodiment, a form of separating the product into a gas component containing components having 4 or fewer carbon atoms (for example, hydrogen, methane, ethane, and LPG) and a liquid fraction, and also, further separating the liquid fraction into a fraction containing monocyclic aromatic hydrocarbons having 6 to 8 carbon atoms and a fraction heavier than this (heavy fraction having 9 or more carbon atoms), is suitably employed.

In addition, in the separation step in which the distillation apparatus or the gas-liquid separation apparatus is used, cooling is carried out in order to condense a portion of the hydrogenation product obtained in the hydrogenation reaction step, thereby separating gas and liquid. However, in the present Embodiment, basically, since a treatment requiring reheating, for example, the hydrogenation reaction step, is not carried out on the respective components separated as described below, thermal loss is rarely caused, and therefore the step becomes a method with a high thermal efficiency.

<Monocyclic Aromatic Hydrocarbon Recovery Step>

In the monocyclic aromatic hydrocarbon recovery step, the monocyclic aromatic hydrocarbons having 6 to 8 carbon atoms obtained in the separation step are collected.

In this monocyclic aromatic hydrocarbon recovery step, since a fraction heavier than the monocyclic aromatic hydrocarbons is separated in the separation step, a step of recovering benzene/toluene/xylene from the fraction containing monocyclic aromatic hydrocarbons having 6 to 8 carbon atoms is employed.

Further, when a form in which a liquid fraction is not fractionated is employed as the separation step, in this monocyclic aromatic hydrocarbon recovery step, a step of separating and removing the fraction heavier than monocyclic aromatic hydrocarbons, and recovering monocyclic aromatic hydrocarbons or benzene/toluene/xylene (monocyclic aromatic hydrocarbons having 6 to 8 carbon atoms) is employed.

Furthermore, when the liquid fraction is not fractionated satisfactorily in the separation step, and when monocyclic aromatic hydrocarbons having 6 to 8 carbon atoms are collected, a fraction other than the monocyclic aromatic hydrocarbons is contained in a large amount, this fraction may be separated and supplied to, for example, the recycling step that will be described below. The fraction heavier than the monocyclic aromatic hydrocarbons contains polycyclic aromatic hydrocarbons as main components, and contains bicyclic aromatic hydrocarbons such as naphthalenes.

<Heavy Fraction Discharge Step>

In a heavy fraction discharge step, a certain amount of a portion of the heavy fraction having 9 or more carbon atoms obtained from the fraction separated in the separation step is taken out, and discharged out of the system.

In the case where the heavy fraction discharge step is not included, components with a low reactivity increase in the heavy fraction as the recycling amount increases, but the present Embodiment includes the heavy fraction discharge step and discharges a certain amount of the heavy fraction, and therefore the increase in the components with a low reactivity in the heavy fraction can be suppressed.

Therefore, a decrease over time in the yield of the monocyclic aromatic hydrocarbons can be prevented.

However, the amount of the heavy fraction discharged out of the system is preferably set to 90% by mass or less of the heavy fraction, more preferably set to 50% by mass or less, and even more preferably set to 20% by mass or less. If the amount of the heavy fraction discharged out of the system is set to 90% by mass of the heavy fraction, since the heavy fraction can be sufficiently recycled, the yield of the monocyclic aromatic hydrocarbons can be further increased.

As the heavy fraction discharged out of the system, heavier hydrocarbons are preferably taken out. For example, since it is difficult to convert a fraction containing a large amount of tricyclic aromatic hydrocarbons to monocyclic aromatic hydrocarbons compared with other fractions even when recycled, a decrease over time in the yield of the monocyclic aromatic hydrocarbons can be prevented by discharging the fraction out of the system. In addition, the heavy fraction being discharged out of the system can be used for fuel base materials and the like.

<Hydrogen Recovery Step>

In the hydrogen recovery step, hydrogen is collected from the gas component obtained in the separation step.

Regarding the method of recovering hydrogen, there are no particular limitations as long as hydrogen and other gases that are contained in the gas component obtained in the separation step can be separated, and examples thereof include a pressure swing adsorption method (PSA method), a cryogenic separation method, and a membrane separation method.

<Hydrogen Supply Step>

In the hydrogen supply step, hydrogen obtained in the hydrogen recovery step is supplied to the hydrogenation reactor of the hydrogenation reaction step. The amount of hydrogen supply at that time is regulated depending on the amount of the product that is supplied to the hydrogenation reaction step, particularly, the amount of hydrogen in the product. In addition, in the hydrogenation reaction step, since hydrogen in the product produced in the cracking reforming reaction step is used as described above, at least a portion of the polycyclic aromatic hydrocarbons in the product can be hydrogenation-reacted. Therefore, in the present Embodiment, since the hydrogen pressure is regulated for the purpose of mitigating the severity of the hydrogenation reaction conditions or increasing the reaction efficiency, the collected hydrogen is supplied to the hydrogenation reaction step.

<Recycling Step>

In the recycling step, the heavy fraction having 9 or more carbon atoms that is separated in the separation step, but is not discharged out of the system in the heavy fraction discharge step is further is mixed with the oil feedstock or is returned to the cracking reforming reaction step.

By returning the heavy fraction to the cracking reforming reaction step, the heavy fraction which is a by-product can also be used as a raw material to obtain monocyclic aromatic hydrocarbons. Therefore, not only the amount of by-products can be reduced, but also the amount of production of monocyclic aromatic hydrocarbons can be increased. Furthermore, since saturated hydrocarbons are also produced by hydrogenation in the hydrogenation reaction step, the hydrogen transfer reaction in the cracking reforming reaction step can be accelerated. From these, the overall yield of monocyclic aromatic hydrocarbons with respect to the amount of supply of the oil feedstock can be enhanced.

In addition, in the case where the hydrogenation treatment through the hydrogenation reaction step is not carried out, and the heavy fraction obtained in the separation step is returned to the cracking reforming reaction step as it is, since the reactivity of the polycyclic aromatic hydrocarbons is low, the yield of the monocyclic aromatic hydrocarbons rarely improves.

Since the method for producing aromatic hydrocarbons of the present Embodiment includes the hydrogenation reaction step and the recycling step, monocyclic aromatic hydrocarbons can be obtained by using a heavy fraction which is a by-product as a raw material. Therefore, not only the amount of by-products can be reduced, but also the amount of production of monocyclic aromatic hydrocarbons can be increased. Therefore, monocyclic aromatic hydrocarbons having 6 to 8 carbon atoms can be produced with a high yield from an oil feedstock containing polycyclic aromatic hydrocarbons.

In addition, for example, as described in the knowledge above, in the case where an oil feedstock is supplied to the cracking reforming reaction step, the produced product is separated in the separation step and the obtained heavy fraction having 9 or more carbon atoms is hydrogenated in the same manner as in the hydrogenation reaction step of the present Embodiment, since the heavy fraction having 9 or more carbon atoms is reheated in the hydrogenation reaction step after once cooled, when the heavy fraction having 9 or more carbon atoms is separated, thermal loss is caused, and the thermal efficiency decreases.

In contrast to what has been described above, in the present Embodiment, separation is not carried out in the former phase of the hydrogenation reaction step, and separation is first carried out in the latter phase of the hydrogenation reaction step. Therefore the thermal efficiency can be increased by reducing thermal loss compared with the case where the separation is carried out, and then a hydrogenation reaction is carried out.

In addition, in the production method in which the cracking reforming reaction step, the separation step and the hydrogenation reaction step are sequentially carried out as described as the knowledge above, separately from the separation of the heavy fraction having 9 or more carbon atoms in the separation step, the separation of monocyclic aromatic hydrocarbons having 6 to 8 carbon atoms is considered. However, in that case, in a step of recovering the separated monocyclic aromatic hydrocarbons (monocyclic aromatic hydrocarbon recovery step), it is necessary to carry out hydrogenation purification in order to remove a small amount of olefin or sulfur. Then, both the hydrogenation reaction step for carrying out the hydrogenation purification and the hydrogenation reaction step of hydrogenating the heavy fraction having 9 or more carbon atoms (hydrogenation reaction step) become necessary, and two hydrogenation reaction steps become necessary, which makes the steps complicated and also increases the scale of the entire apparatus configuration.

In contrast to what has been described above, since the present Embodiment includes the hydrogenation reaction step before the separation step, the small amount of olefin or sulfur is removed in this step, and therefore monocyclic aromatic hydrocarbons having 6 to 8 carbon atoms separated in the separation step do not include olefin or sulfur. Therefore, it is not necessary to separately provide a step for carrying out hydrogenation purification in the former phase of the monocyclic aromatic hydrocarbon recovery step, whereby it is possible to avoid the complication of the steps and an increase in the scale of the entire apparatus configuration.

In addition, in the production method in which the cracking reforming reaction step, the separation step and the hydrogenation reaction step are sequentially carried out as described as the knowledge above, since only the heavy fraction having 9 or more carbon atoms separated in the separation step is hydrogenated in the hydrogenation reaction step, the control of heat generation becomes difficult. That is, the polycyclic aromatic hydrocarbons contained in a large amount in the heavy fraction having 9 or more carbon atoms (mainly bicyclic aromatic hydrocarbons) generate an extremely large amount of heat during the hydrogenation reaction. Therefore, when only the heavy fraction having 9 or more carbon atoms containing a large amount of the polycyclic aromatic hydrocarbons (bicyclic aromatic hydrocarbons) is hydrogenation-reacted, the control of the heat generation is extremely difficult, and the configuration of an apparatus for the control of heat generation also becomes extremely complicated.

In contrast to what has been described above, in the present Embodiment, the product produced in the cracking reforming reaction step is not separation-treated, and therefore the product is hydrogenation-reacted in a state in which not only the heavy fraction having 9 or more carbon atoms but also monocyclic aromatic hydrocarbons having 6 to 8 carbon atoms are included. Then, since monocyclic aromatic hydrocarbons having 6 to 8 carbon atoms are rarely hydrogenated in the hydrogenation reaction step, heat is not generated. Therefore, the monocyclic aromatic hydrocarbons function as a diluent that dilutes polycyclic aromatic hydrocarbons (bicyclic aromatic hydrocarbons). That is, the heat generation in the hydrogenation reactor is suppressed by the dilution effect of the monocyclic aromatic hydrocarbons having 6 to 8 carbon atoms. Thereby, in the present Embodiment, heat generation is suppressed in the hydrogenation reaction step, and therefore the disadvantage of the apparatus configuration of the hydrogenation reactor becoming extremely complicated can be avoided.

Modified Example of Embodiment 1

In Embodiment 1, the entire amount of the oil feedstock is supplied to the cracking reforming reaction step; however, as illustrated in FIG. 1, a portion of the oil feedstock may be directly supplied to the hydrogenation reaction step.

That is, an oil feedstock mixing step in which a portion of the oil feedstock is mixed with the product produced in the cracking reforming reaction step may be provided.

The concentration of the polycyclic aromatic hydrocarbons in the mixed oil which will be treated in the subsequent hydrogenation reaction step can be decreased compared with the case of Embodiment 1 where the entire amount of the oil feedstock is supplied to the cracking reforming reaction step by mixing a portion of the oil feedstock with the product produced in the cracking reforming reaction step so as to produce a mixed oil in the raw material mixing step. That is, in the cracking reforming reaction step, since bicyclic aromatic hydrocarbons (polycyclic aromatic hydrocarbons) are produced as by-products as described above, the concentration of the polycyclic aromatic hydrocarbons becomes high compared with the oil feedstock. Therefore, the heat generation in the hydrogenation reactor can be suppressed using the dilution effect of the oil feedstock by mixing a portion of the oil feedstock with the product produced in the cracking reforming reaction step as a diluent and causing a hydrogenation reaction of the mixed oil in the hydrogenation reaction step.

That is, a large amount of heat generation occurs due to the hydrogenation reaction of the polycyclic aromatic hydrocarbons (bicyclic aromatic hydrocarbons) in the hydrogenation reaction step; however, since the product containing the monocyclic aromatic hydrocarbons having 6 to 8 carbon atoms that function as the diluent as described above is supplied to the hydrogenation reaction step, and the product is further diluted by the oil feedstock, the heat generation in the hydrogenation reactor can be sufficiently suppressed. Thereby, in the present modified example, heat generation is suppressed in the hydrogenation reaction step, and therefore the disadvantage of the apparatus configuration of the hydrogenation reactor becoming extremely complicated can be avoided.

Embodiment 2

Embodiment 2 of the method for producing monocyclic aromatic hydrocarbons of the invention will be described.

Figure 2:
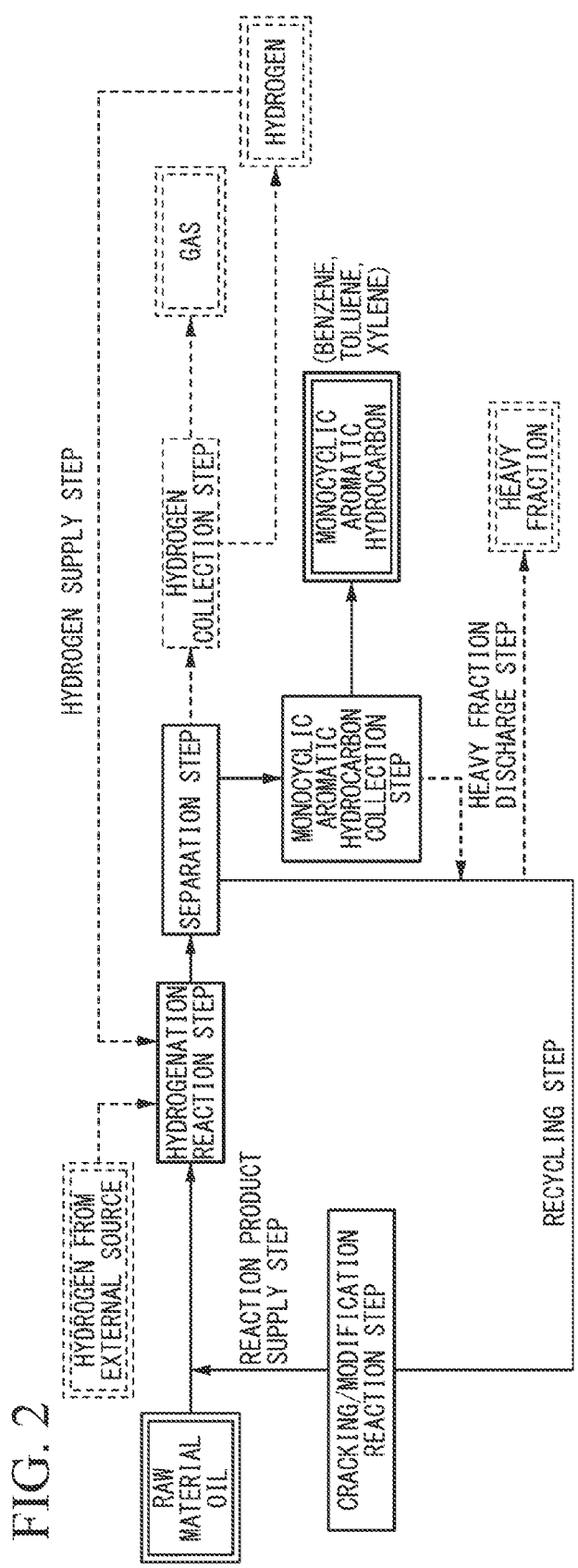
FIG. 2 is a diagram for illustrating Embodiment 2 of the method for producing monocyclic aromatic hydrocarbons of the invention.

FIG. 2 is a diagram for illustrating Embodiment 2 of the method for producing monocyclic aromatic hydrocarbons of the invention, and the method for producing monocyclic aromatic hydrocarbons of the present Embodiment is also a method for producing monocyclic aromatic hydrocarbons having 6 to 8 carbon atoms from an oil feedstock.

That is, the method for producing monocyclic aromatic hydrocarbons of the present Embodiment includes, as illustrated in FIG. 2:

(i) a hydrogenation reaction step of hydrogenating an oil feedstock;

(j) a separation step of separating a hydrogenation product obtained in the hydrogenation reaction step into plural fractions;

(k) a monocyclic aromatic hydrocarbon recovery step of recovering monocyclic aromatic hydrocarbons having 6 to 8 carbon atoms separated in the separation step;

(l) a heavy fraction discharge step of discharging a portion of a heavy fraction having 9 or more carbon atoms (hereinafter referred to simply as "heavy fraction") separated in the separation step out of the system;

(m) a recycling step of supplying the heavy fraction not discharged out of the system in the heavy fraction discharge step to the cracking reforming reaction step;

(n) a cracking reforming reaction step of bringing the heavy fraction into contact with a catalyst for monocyclic aromatic hydrocarbon production, and causing the heavy fraction to react, thereby obtaining a product containing monocyclic aromatic hydrocarbons having 6 to 8 carbon atoms;

(o) a reaction product supply step of supplying the product produced in the cracking reforming reaction step to the hydrogenation reaction step together with the oil feedstock;

(p) a hydrogen recovery step of recovering hydrogen that has been produced as a by-product in the cracking reforming reaction step from the gas component separated in the separation step; and (q) a hydrogen supply step of supplying the hydrogen collected in the hydrogen recovery step to the hydrogenation reaction step.

Among the steps (i) to (q), the steps (i), (k), (m), (n) and (o) are essential steps for the Embodiment 2, and the steps (j), (l), (p) and (q) are optional steps.

The hydrogenation reaction step (i) can be carried out in the same manner as the hydrogenation reaction step (b) in Embodiment 1. However, in the present Embodiment, since the entire amount of the oil feedstock is directly supplied to the hydrogenation reaction step, the product in the cracking reforming reaction step is mixed with the oil feedstock by the reaction product supply step that will be described below, but the concentration of polycyclic aromatic hydrocarbons (bicyclic aromatic hydrocarbons) in the oil that is supplied to the hydrogenation reaction step decreases compared with in the modified example of Embodiment 1. That is, the dilution amount by the oil feedstock increases. Therefore, in the hydrogenation reaction step, since the dilution effect of the oil feedstock becomes more favorable than in Embodiment 1 or the modified example, the heat generation in the hydrogenation reactor is more sufficiently suppressed.

The separation step (j) can be carried out in the same manner as the separation step (c) in Embodiment 1.

The monocyclic aromatic hydrocarbon recovery step (k) can be carried out in the same manner as the monocyclic aromatic hydrocarbon recovery step (d) in Embodiment 1.

The heavy fraction discharge step (l) can be carried out in the same manner as the heavy fraction discharge step (e) in Embodiment 1.

In the recycling step (m), the heavy fraction not discharged out of the system in the heavy fraction discharge step is supplied to the cracking reforming reaction step, similarly to the recycling step (f) in Embodiment 1.

The cracking reforming reaction step (n) can be carried out in the same manner as the cracking reforming reaction step (a) in Embodiment 1. However, in the cracking reforming reaction step of the present Embodiment, since the oil that is supplied by the recycling step has already passed through the hydrogenation reaction step, the oil has a portion of the polycyclic aromatic hydrocarbons in the oil feedstock converted through the hydrogenation reaction to naphthenobenzenes, that is, aromatic hydrocarbons having one aromatic ring with a tetraline skeleton as described in the hydrogenation reaction step of Embodiment 1. The naphthenobenzenes are easily converted to monocyclic aromatic hydrocarbons in the cracking reforming reaction step. Therefore, in the cracking reforming reaction step of the present Embodiment, the oil containing a large amount of naphthenobenzenes is supplied to the cracking reforming reaction step as an oil to be treated, and therefore the yield of the monocyclic aromatic hydrocarbons increases.

In the reaction product supply step (o), the product produced in the cracking reforming reaction step is mixed with the oil feedstock, and supplied to the hydrogenation reaction step. The mixing ratio between the product and the oil feedstock is preferably in a range of 20:80 to 80:20 by mass ratio.

The hydrogen recovery step (p) can be carried out in the same manner as the hydrogen recovery step (g) in Embodiment 1.

The hydrogen supply step (q) can be carried out in the same manner as the hydrogen supply step (h) in Embodiment 1.

In the present Embodiment, when the oil feedstock is first supplied to the hydrogenation reaction step at the time of the beginning of the production, unlike Embodiment 1, the oil feedstock does not contain hydrogen necessary for the hydrogenation reaction step.

Therefore, it is necessary to introduce hydrogen into the hydrogenation rector from an external source; however, at this time, the hydrogen recovery step is also not in operation, and therefore it is not also possible to supply hydrogen to the hydrogenation reactor by the hydrogen supply step. Therefore, in the present Embodiment, at the time of the beginning of the production, hydrogen is supplied from a hydrogen supply source outside the system through a pipe or the like connected in advance to the hydrogenation reactor. In addition, in the case where hydrogen obtained in the hydrogen recovery step has remained and has been stored in a tank or the like at the time of the earlier production than the time of the present production, the hydrogen may be supplied to the hydrogenation reactor using the hydrogen supply step.

In addition, after the beginning of the production, if the initial oil feedstock passes through the recycling step and is cracked/modified in the cracking reforming reaction step, and the product is supplied to the hydrogenation reaction step together with the oil feedstock, since hydrogen is sufficiently contained in the product as described above, the hydrogenation reaction proceeds in the hydrogenation reaction step using hydrogen in the product. However, the supply of hydrogen using the hydrogenation reaction step or the supply of hydrogen from the outside of the system may be carried out as necessary.

Even the method for producing aromatic hydrocarbons of the present Embodiment includes the hydrogenation reaction step and the recycling step, monocyclic aromatic hydrocarbons having 6 to 8 carbon atoms can be produced from an oil feedstock including polycyclic aromatic hydrocarbons with a high yield.

In addition, particularly, since the hydrogenation reaction step is provided before the cracking reforming reaction step, an oil containing a large amount of naphthenobenzenes produced by the hydrogenation reaction step is supplied to the cracking reforming reaction step, and therefore the yield of monocyclic aromatic hydrocarbons by the cracking reforming reaction increases. Therefore, the yield of the monocyclic aromatic hydrocarbons having 6 to 8 carbon atoms which are finally obtained can be further increased.

Furthermore, since the entire amount of the oil feedstock is directly supplied to the hydrogenation reaction step, the product that is obtained in the cracking reforming reaction step can be diluted by the oil feedstock, and therefore the heat generation in the hydrogenation reactor can be further suppressed. Therefore, heat generation is suppressed in the hydrogenation reaction step, and the disadvantage of the apparatus configuration of the hydrogenation reactor becoming extremely complicated can be avoided.

Furthermore, similarly to Embodiment 1, in the present Embodiment as well, since separation is not carried out in the former phase of the hydrogenation reaction step and separation is first carried out in the latter phase of the hydrogenation reaction step, the thermal efficiency can be increased by reducing thermal loss compared with the case where the separation is carried out and then a hydrogenation reaction is carried out.

In addition, similarly to Embodiment 1, in the present Embodiment as well, since the hydrogenation reaction step can also serve as the hydrogenation reaction step (hydrogenation purification) for removing a small amount of olefin or sulfur in the oil feedstock, it is not necessary to separately provide a step for carrying out hydrogenation purification in the former phase of the monocyclic aromatic hydrocarbon recovery step, whereby it is possible to avoid the complication of the steps and an increase in the scale of the entire apparatus configuration.

Other Embodiments

The present invention is not intended to be limited to the Embodiments, and various modifications can be made to the extent that the gist of the invention is maintained.

For example, regarding the hydrogen to be used in the hydrogenation reaction step, not the hydrogen produced as a by-product in the cracking reforming reaction step, but hydrogen that is obtained by a known hydrogen production method may be utilized.

EXAMPLES

Hereinafter, the present invention will be described more specifically based on Examples and Comparative Examples, but the invention is not intended to be limited to these Examples.

Example 1

As a raw material, LCO (10 vol % distillation temperature: 226.5° C., 90 vol % distillation temperature: 350.0° C.) was brought into contact with a catalyst A (containing a binder in MFI type zeolite having 0.4 mass % of gallium and 0.7 mass % of phosphorus supported thereon) in a fluidized bed reactor under conditions of reaction temperature: 538° C., reaction pressure: 0.3 MPaG, and a contact time for contact between the LCO and the zeolite component contained in the catalyst of 12 seconds, and was allowed to react. Thus, a cracking reforming reaction was carried out. The recovery rate of a liquid fraction was 79% by mass with respect to the oil feedstock (LCO) supplied to the fluidized reactor, the yield of BTX (benzene, toluene and xylene) was 35% by mass with respect to the oil feedstock (LCO), and a fraction heavier than the BTX fraction was, similarly, 44% by mass. In addition, the hydrogen concentration in gas in a product of the cracking reforming reaction was 52 mol % (molar fraction). In addition, the main component other than hydrogen was methane, and the product additionally contained ethane, propane and the like. The proportion of polycyclic aromatic hydrocarbons in the fraction heavier than BTX was 87% by mass.

Next, the obtained reaction product was subjected to a hydrogenation treatment in a hydrogenation reactor under conditions of reaction pressure: 7 MPa and reaction temperature: 360° C.

Next, a liquid collected from the hydrogenation reactor was separated into a fraction containing BTX and a heavy fraction heavier than BTX, 42% by mass of the BTX fraction and 56% by mass of the heavy fraction were obtained. In addition, the amount of the polycyclic aromatic hydrocarbon in the heavy fraction was 38% by mass.

After that, the obtained hydrogenated heavy fraction was, again, supplied to the cracking reforming reaction step, and a cracking reforming reaction is carried out. As a result, the yield of BTX was 39% by mass.

Example 2

In Example 1, the reaction product obtained in the cracking reforming reaction was put into the hydrogenation reactor, then, separately from the reaction product, hydrogen was added so as to obtain a hydrogen concentration in the gas of 80 mol % (molar fraction), and then a hydrogenation treatment was carried out under conditions of reaction pressure: 7 MPa and reaction temperature: 360° C. Except for what has been described above, the steps were carried out in the same manner as in Example 1. As a result, the yield of BTX was 42% by mass.

Example 3

In Example 1, the reaction product obtained in the cracking reforming reaction was put into the hydrogenation reactor to which 100 parts by weight of LCO, which was the oil feedstock, with respect to 100 parts by weight of the reaction product had been added in advance, then, hydrogen was further added so as to obtain a hydrogen concentration in the gas of 80 mol % (molar fraction), and a hydrogenation treatment was carried out under conditions of reaction pressure: 7 MPa and reaction temperature: 360° C. Except for what has been described above, the steps were carried out in the same manner as in Example 1. As a result, the yield of BTX was 40% by mass.

Comparative Example 1

In Example 1, the reaction product obtained in the cracking reforming reaction was directly collected without being hydrogenated, a heavy fraction having 9 or more carbon atoms was obtained from a collected liquid through distillation, and the heavy fraction was again supplied to the cracking reforming reaction step, thereby carrying out a cracking reforming reaction. Except for what has been described above, the steps were carried out in the same manner as in Example 1. As a result, the yield of BTX was 7% by mass.

From the above results, it was confirmed that, even when the reaction product obtained in the cracking reforming reaction step is hydrogenation-reacted without being separated, monocyclic aromatic hydrocarbons having 6 to 8 carbon atoms can be efficiently produced.

The invention claimed is:

1. A method for producing monocyclic aromatic hydrocarbons having 6 to 8 carbon atoms from an oil feedstock having a 10 vol % distillation temperature of 140° C. or higher and a 90 vol % distillation temperature of 380° C. or lower, the method comprising:
    a cracking reforming reaction step of bringing the oil feedstock into contact with a catalyst for monocyclic aromatic hydrocarbon production containing a crystalline aluminosilicate, and causing the oil feedstock to react, thereby obtaining a product containing monocyclic aromatic hydrocarbons having 6 to 8 carbon atoms, a heavy fraction having 9 or more carbon atoms including polycyclic aromatic hydrocarbons, hydrogen, methane, ethane, ethylene and LPG;
    a hydrogenation reaction step of hydrogenating the product produced in the cracking reforming reaction step;
    a monocyclic aromatic hydrocarbon recovery step of recovering monocyclic aromatic hydrocarbons having 6 to 8 carbon atoms separated from a hydrogenation product obtained in the hydrogenation reaction step; and
    a recycling step of returning a heavy fraction having 9 or more carbon atoms separated from the hydrogenation product obtained in the hydrogenation reaction step to the cracking reforming reaction step,
        wherein, in the hydrogenation reaction step, the product produced in the cracking reforming reaction step is subjected to hydrogenation without separating the monocyclic aromatic hydrocarbons having 6 to 8 carbon atoms from the product, such that a concentration of the polycyclic aromatic hydrocarbons decreases and heat generation is suppressed in the hydrogenation reaction step.

2. The method for producing monocyclic aromatic hydrocarbons according to claim 1, further comprising:
    a raw material mixing step of mixing a portion of the oil feedstock with the product produced in the cracking reforming reaction step.

3. The method for producing monocyclic aromatic hydrocarbons according to claim 1,
    wherein the crystalline aluminosilicate contained in the catalyst for monocyclic aromatic hydrocarbon production used in the cracking reforming reaction step contains a medium-pore zeolite and/or a large-pore zeolite as main components.

4. The method for producing monocyclic aromatic hydrocarbons according to claim 1, further comprising:
    a hydrogen recovery step of recovering hydrogen produced as a by-product in the cracking reforming reaction step from the hydrogenation product obtained in the hydrogenation reaction step; and
    a hydrogen supply step of supplying the hydrogen collected in the hydrogen recovery step to the hydrogenation reaction step.

5. The method for producing monocyclic aromatic hydrocarbons according to claim 1, wherein a reaction temperature in the cracking reforming reaction step is set to 50 to 400° C. higher than a reaction temperature in the hydrogenation reaction step.

6. The method for producing monocyclic aromatic hydrocarbons according to claim 1, wherein an amount of aromatic hydrocarbons having three or more rings in the oil feedstock is 25 vol % or less.

* * * * *